United States Patent
Garcia et al.

(10) Patent No.: US 6,945,473 B2
(45) Date of Patent: Sep. 20, 2005

(54) FLUID PRODUCT DISPENSER

(75) Inventors: Firmin Garcia, Evreux (FR); Jean-Paul Lecoutre, Breteuil sur Iton (FR); Alex Millan, Breteuil/Iton (FR)

(73) Assignee: Valois S.A.S. (FR)

( * ) Notice: Subject to any disclaimer, the term of this patent is extended or adjusted under 35 U.S.C. 154(b) by 0 days.

(21) Appl. No.: 10/320,631

(22) Filed: Dec. 17, 2002

(65) Prior Publication Data

US 2003/0080198 A1 May 1, 2003

Related U.S. Application Data

(60) Provisional application No. 60/350,028, filed on Jan. 23, 2002.

(30) Foreign Application Priority Data

Dec. 20, 2001 (FR) .............................. 01 16553

(51) Int. Cl.[7] .......................... B65D 1/32; B65D 32/00; B05B 9/00
(52) U.S. Cl. ......................... 239/327; 239/326; 239/44; 222/211
(58) Field of Search ........................... 239/44, 327, 37, 239/302, 328, 326; 222/211, 212

(56) References Cited

U.S. PATENT DOCUMENTS

| | | | | |
|---|---|---|---|---|
| 3,361,304 A | * | 1/1968 | Thompson | .................. 222/190 |
| 3,985,271 A | * | 10/1976 | Gardner | ...................... 222/190 |
| 4,027,789 A | * | 6/1977 | Dickey | ....................... 222/190 |
| 4,147,306 A | * | 4/1979 | Bennett | ...................... 239/327 |
| 4,184,615 A | * | 1/1980 | Wright | ....................... 222/190 |
| 4,274,594 A | * | 6/1981 | Ito | .............................. 239/327 |
| 4,432,496 A | | 2/1984 | Ito | |
| 5,364,027 A | * | 11/1994 | Kuhn | .......................... 239/44 |

FOREIGN PATENT DOCUMENTS

| | | |
|---|---|---|
| FR | 1.525.560 A | 5/1968 |
| FR | 2 610 302 A | 8/1988 |

\* cited by examiner

*Primary Examiner*—David A. Scherbel
*Assistant Examiner*—Darren Gorman
(74) *Attorney, Agent, or Firm*—Sughrue Mion, PLLC

(57) ABSTRACT

The invention relates to a fluid product dispenser having a reservoir (1) containing a fluid product and a gas, and having an opening (15), a bottom (13), and an actuation wall (11) that is movable to reduce the volume of the reservoir. The dispenser also has a dispensing orifice (22), a plunger tube (4) that extends into the reservoir, and a porous material part (3) that absorbs fluid product by capillary action, and which is placed between the plunger tube and the dispensing orifice (22). The porous material part has a discharge end (31) located in the immediate vicinity of the dispensing orifice (22).

14 Claims, 1 Drawing Sheet

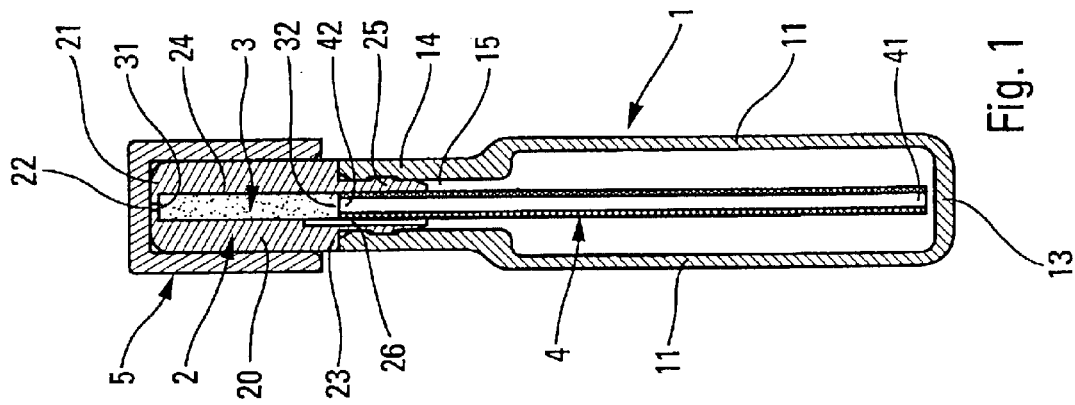
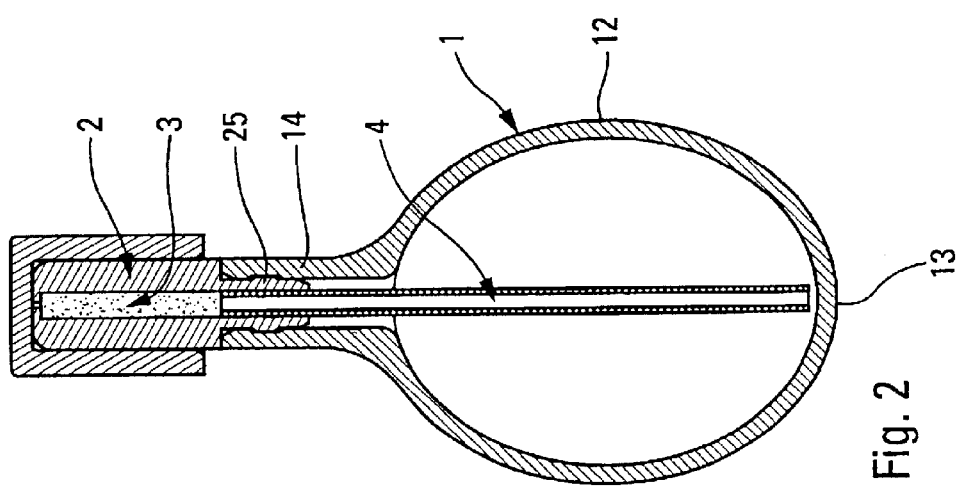
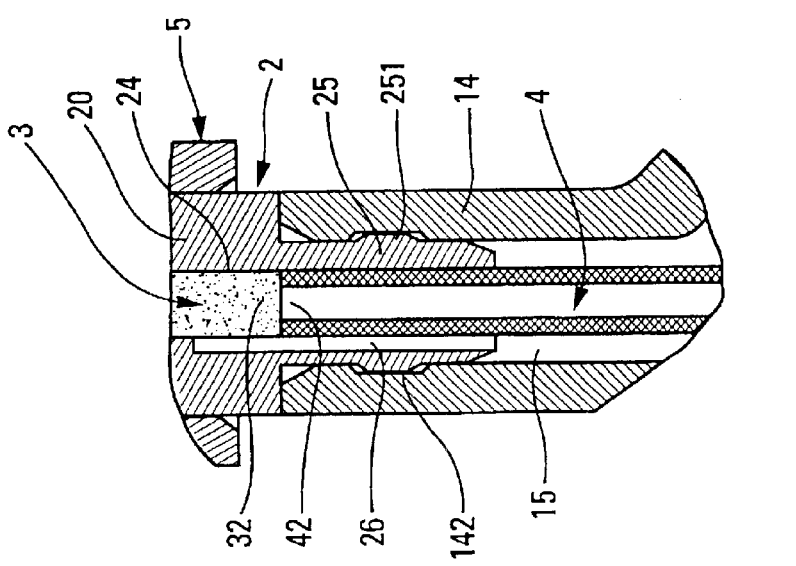

FLUID PRODUCT DISPENSER

CROSS REFERENCE TO RELATED APPLICATION

This application claims the benefit under 35 U.S.C. §119 (e) of now abandoned U.S. provisional patent application Ser. No. 60/350,028, filed Jan. 23, 2002, and priority under 35 U.S.C. §119(a)-(d) of French patent application No. FR-01.16553, filed Dec. 20, 2001.

FIELD OF INVENTION

This invention relates to a fluid product dispenser comprising a reservoir containing fluid product and a gas, the said reservoir comprising an opening, a bottom and an actuation wall that can be moved to reduce the volume of the reservoir, a dispensing orifice through which the fluid product is distributed each time that the actuation wall is actuated, and a part made of a porous material capable of absorbing fluid product by capillarity being placed in the immediate vicinity of the dispensing orifice with a discharge end.

BACKGROUND OF THE INVENTION

In particular, such a dispenser is described in documents U.S. Pat. No. 4,858,831 and FR-2 781 770. Both documents describe a dispenser in the form of a fluid product sample for the cosmetics, perfume or pharmaceutical industry.

In the prior art mentioned above, the porous material part extends into the fluid product reservoir so that it is free to absorb the fluid product by capillarity. The porous material part thus contains a certain quantity that depends on its absorption capacity. After the wall has been actuated several times, the porous material part will no longer contain any of the fluid product that it had absorbed. Depending on the orientation of the dispenser, it is possible that the porous material part is not in contact with the fluid product stored inside the reservoir. In this case, the fluid product is emptied out of the porous material part after the wall has been actuated a number of times, such that the dispenser distributes mostly air and only a very small quantity of the fluid product.

SUMMARY OF THE INVENTION

This invention is intended to solve or alleviate the above mentioned problem related to filling the porous material part with a fluid product after each actuation.

FR-1 525 560 describes a dispenser comprising a reservoir with deformable walls, a dispensing orifice, a plunger tube and a porous material part. However, an intermediate chamber is present between the porous material part and the dispensing orifice: its function is not mentioned in the document. Empirically, it has been observed that the presence of a chamber between the porous part and the dispensing orifice leads in some cases to collecting of fluid product in this chamber, so that the distribution is a fluid product jet and not a two phase spray.

The present invention has also to overcome this problem.

In order to achieve this, the porous material part has a discharge end located in the immediate vicinity of the dispensing orifice. Although a conventional plunger tube is normally used with a dispensing device such as a pump or a valve to transport the fluid product into the pump or valve chamber, in this case the same element (plunger tube) is used to supply the porous material part that acts as a sort of a buffer reservoir in the immediate vicinity of the dispensing orifice. Advantageously, the connection end of the plunger tube is in contact with the porous material part.

According to one particularly interesting characteristic of this invention, at least one passage connects the porous material part to the reservoir without passing through the plunger tube, such that the gas and fluid product are simultaneously flushed through the porous material part every time that the actuation wall is actuated. This is true in almost any position of the dispenser; whenever the dispenser is kept upright with its dispensing orifice facing upwards, the fluid product is stored in the bottom of the reservoir and the plunger tube then forces the fluid product towards the porous material part while gas, advantageously air, is transferred through the passage to the same porous material part. Conversely, when the dispensing orifice is facing downwards, the fluid product is stored close to its opening such that the passage carries the fluid product to the porous material part, whereas the plunger tube can allow air to pass since its free end is not immersed in the fluid product. Advantageously, the passage extends partially along the plunger tube.

According to a practical embodiment, the dispensing orifice is formed by an end piece fitted on the opening of the reservoir, the said end piece forming a reception housing in which the porous material part is engaged. Advantageously, the end piece forms an attachment sleeve with which the plunger tube comes into contact with its connection end. Advantageously, the attachment sleeve may grip in the reservoir opening. Preferably, the said at least one passage is formed inside the sleeve and extends as far as the reception housing.

One practical embodiment could be that the end piece comprises a body defining a dispensing end forming the dispensing orifice and an opposite attachment end fitted with an attachment sleeve to which the plunger tube is connected, the inside of the said body forming the reception housing for the porous material part, the said housing and the said sleeve being aligned with each other such that the connection end of the plunger tube can come into contact with the porous material part.

The concept of this invention is that a conventional plunger tube, which may be in the form of a length of a circular tube, is associated with a porous material part in the vicinity of the dispensing orifice. This combination may advantageously be completed by a direct passage towards the porous material part that can carry either a fluid product or a gas, for example air.

BRIEF DESCRIPTION OF THE DRAWINGS

The invention will now be described in more detail with reference to the attached drawings given as a non-limitative example of an embodiment of the invention.

On the figures:

FIG. 1 shows a vertical cross-sectional view of a profile through the fluid product dispenser according to this invention, FIG. 2 is a view similar to FIG. 1, showing the front face and, FIG. 3 is an enlarged view of the upper part of the dispenser in FIG. 1.

PREFERRED EMBODIMENTS OF THE INVENTION

The dispenser is shown in full in FIGS. 1 and 2, and includes a reservoir 1, a dispensing end piece 2, a porous material part 3, a plunger tube 4 and optionally a cap 5.

The reservoir 1 comprises a bottom 13 and side walls 11 and 12. It can be seen that the side walls 12 are curved or rounded and are joined together at their bottom to form the bottom wall 13. At least one of the other two side walls 11 forms a push-in actuation wall, which is deformable so that the internal volume of the reservoir can be varied. Thus, the user can press on the actuation wall 11 with a finger or even better a thumb, to force it inwards towards the other side wall 11, which has the effect of reducing the internal volume of the reservoir. The reservoir 1 also forms a neck 14 defining an opening 15 that forms a passageway between the inside of the reservoir and the outside. Advantageously, the inside wall of the neck 14 may be fitted with a recess 142, for which the attachment or support function will be described later.

The specific shape of the reservoir described in this document must not be considered as being limitative. On the contrary, it would be possible to imagine a reservoir with an arbitrary shape but with at least one actuation wall that could be pressed in or deformed.

Depending on the embodiment of the invention, the end piece 2 is installed on, or more precisely in the opening 15 formed by the neck 14 of the reservoir 1. The end piece 2 defines a dispensing orifice 22. Thus, the fluid product stored inside the reservoir 1 can be discharged through the dispensing orifice 22 formed by the end piece 2 when pressing on the actuation wall 11 in order to reduce the internal volume of the reservoir. According to the invention, the reservoir contains a small quantity of fluid product, the remaining amount of the reservoir volume being filled with a gas, preferably air. In this way, a mix of the fluid product and air is discharged through the dispensing orifice 22 when the actuation wall 1 is pressed. The result is a two-phase sprayed jet of fluid and air.

As shown on the figures, the end piece 2 may be in the form of a body 20 with a dispensing end 21 in which the dispensing orifice 22 is formed, and an opposite attachment end 23 from which an attachment sleeve 25 is fitted extending inside the opening 15 formed by the neck 14 of the reservoir. With reference to FIG. 3, it can be seen that the sleeve 25 forms one or several click fit profile(s) 251 that will fit inside the recess 142 formed in the inside wall of the neck 14. Therefore it is very easy to install the end piece 2 on the reservoir 1; all that is necessary is to insert the sleeve 25 into the opening 15 of neck 14 and to apply sufficient pressure to the end piece 2 to force it to penetrate into the opening 15. In the final position shown enlarged in FIG. 3, the click fit profile(s) 251 click fit into the recess 142. This provides a perfectly firm attachment of the end piece 2 onto the reservoir 1.

According to the invention, the end piece 2 forms an internal reception housing 24 that extends between the sleeve 25 and the dispensing orifice 22. This reception orifice 24 according to the invention contains a porous material part 3 designed to absorb fluid product by capillarity. This porous material part may be made from a foam or fiber that defines an internal network of ducts with a small cross-section to enable absorption by capillarity. The porous material part 3 comprises a discharge end 31 located adjacent to, or in the immediate vicinity of or tightly close to, the dispensing orifice 22 and a supply end 32 located approximately at the position at which the connection sleeve 25 is connected to the body 20. Preferably, the discharge end is in contact with the dispensing end 21 in which the dispensing orifice 22 is formed, so that the discharge end is in contact with the orifice 22. Obviously, the supply end 32 may also be located directly inside the sleeve 25, or may stop in the body 20.

According to the invention, the plunger tube 4 comprises a free end 41 located in the vicinity of the bottom 13 of the reservoir 1 and an opposite connection end 42 in contact with the inside of the attachment sleeve 25. The plunger tube 4 may simply be force fitted into the attachment sleeve 25. Advantageously, the connection end 42 of the plunger tube 4 can come into contact with the supply end 32 of the porous material part 3 as can be seen clearly in FIG. 3. In this way, the fluid product stored at the bottom 13 of reservoir 1 may be forced as far as the porous material part 3 through the plunger tube 4 by pressing on the actuation wall 11. Conversely, if the dispenser is kept approximately upside down with its free end 41 extending outside the fluid product, the porous material part 3 may be supplied with air through the plunger tube 4 by pressing on the actuation wall 11. Since a dispenser is most frequently used with its dispensing orifice 22 higher than the bottom 13 of the reservoir, the plunger tube 4 guarantees that fluid product will always be supplied to the porous material part 3. This guarantees dispensing of the fluid product through the dispensing orifice 22.

According to another interesting characteristic of the invention, the dispenser may also comprise one or several passages 26 that provide a direct passageway between the porous material part and the reservoir 1 without passing through the plunger tube 4. In the embodiment used to illustrate this invention, this passage 26 is formed by the end piece 2 in the form of a chase or a groove that extends inside the sleeve 25 as far as the body 20. Obviously, several passages 26 may be provided, for example distributed around the plunger tube 4 inside the sleeve 25. This or these passages 26 can be used to supply air to the porous material part 3 when the dispenser is kept in contact with its dispensing orifice 22 above its bottom 13. Conversely, when the dispenser is held upside down, the passage(s) 26 enable direct supply of the fluid product to the porous material part. At the same time, the plunger tube 4 provides an air supply.

The use of one or several passages 26 in a dispenser comprising a plunger tube associated with a porous material part 3 provides assurance that the porous material part 3 is always supplied with fluid and with air, regardless of its position. The fluid product can be supplied through the plunger tube and air through the passage, or conversely air may be supplied through the plunger tube and the fluid product through the passage.

Optionally, the end piece 3 may be capped with a cap 5 that closes or conceals the dispensing orifice 22.

The concept of the invention is to combine a conventional plunger tube with a porous material part communicating with the dispensing orifice, a balanced supply of fluid product and air being achieved due to the presence of a passage external to the plunger tube.

What is claimed is:

1. A fluid product dispenser comprising:
   a reservoir (1) containing the fluid product and a gas, the said reservoir comprising an opening (15), a bottom (13), and an actuation wall (11) that can be moved to reduce the volume of the reservoir,
   a dispensing orifice (22) through which the fluid product is sprayed as a jet from the dispenser every time that the actuation wall is actuated, and
   a plunger tube (4) that extends with a free end (41) into the reservoir (1) almost to its bottom (13), the said plunger tube (4) comprising an opposite connection end (42) through which fluid product is supplied to the dispensing orifice, a porous material part (3) that can absorb fluid product by capillarity being placed between the plunger tube and the dispensing orifice (22), wherein the porous material part (3) has a discharge end (31) located in the immediate vicinity of the dispensing orifice (22) so that the fluid product is sprayed as a jet from the dispenser upon actuation of the actuation wall; and wherein the discharge end (31) is in contact with the dispensing orifice.

2. A fluid product dispenser comprising:

a reservoir containing the fluid product and a gas, the said reservoir comprising an opening, a bottom, and an actuation wall that can be moved to reduce the volume of the reservoir, a dispensing orifice through which the fluid product is sprayed as a jet from the dispenser every time that the actuation wall is actuated, and a plunger tube that extends with a free end into the reservoir almost to its bottom, the said plunger tube comprising an opposite connection end through which fluid product is supplied to the dispensing orifice, a porous material part that can absorb fluid product by capillarity being placed between the plunger tube and the dispensing orifice, wherein the porous material part has a discharge end located in the immediate vicinity of the dispensing orifice so that the fluid product is sprayed as a yet from the dispenser upon actuation of the actuation wall; and wherein the connection end of the plunger tube is in contact with the porous material part.

3. Dispenser according to claim 1, wherein at least one passage (26) forms a passageway between the porous material part (3) and the reservoir (1) without passing through the plunger tube (4), such that the gas and the fluid product are simultaneously pushed through the porous material part (3) every time that the actuation wall (11) is pressed.

4. Dispenser according to claim 3, wherein the passage (26) extends partially along the plunger tube (4).

5. Dispenser according to claim 1, wherein the dispensing orifice (22) is formed by an end piece (2) installed on the opening (15) of the reservoir (1), the said end piece (2) forming a reception housing (24) in which the porous material part (3) fits.

6. Dispenser according to claim 5, wherein the end piece (2) forms an attachment sleeve (25) with which the plunger tube (4) comes into contact with its connection end (42).

7. Dispenser according to claim 6, wherein the attachment sleeve (25) is gripped in the reservoir opening (15).

8. Dispenser according to claim 6, wherein at least one passage (26) is formed inside the sleeve (25) and extends as far as the reception housing (24).

9. A fluid product dispenser comprising:

a reservoir containing the fluid product and a gas, the said reservoir comprising an opening, a bottom, and an actuation wall that can be moved to reduce the volume of the reservoir, a dispensing orifice through which the fluid product is sprayed as a jet from the dispenser every time that the actuation wall is actuated, and a plunger tube that extends with a free end into the reservoir almost to its bottom, the said plunger tube comprising an opposite connection end through which fluid product is supplied to the dispensing orifice, a porous material part that can absorb fluid product by capillarity being placed between the plunger tube and the dispensing orifice, wherein the porous material part has a discharge end located in the immediate vicinity of the dispensing orifice so that the fluid product is sprayed as a jet from the dispenser upon actuation of the actuation wall;

wherein the dispensing orifice is formed by an end piece installed on the opening of the reservoir, the end piece forming a reception housing in which the porous material part fits; and wherein the end piece comprises a body defining a dispensing end forming the dispensing orifice and an opposite attachment end provided with an attachment sleeve to which the plunger tube is connected, the inside of the said body forming the reception housing for the porous material part, the said housing and the said sleeve being aligned with each other such that the connection end of the plunger tube can come into contact with the porous material part.

10. A fluid product dispenser comprising:

a reservoir containing the fluid product and a gas, the reservoir comprising an opening, a bottom, and an actuation wall that, when actuated, reduces the volume of the reservoir;

a dispensing orifice through which the fluid product is sprayed as a jet when the actuation wall is actuated;

a tube that extends with a free end into the reservoir, the tube comprising an opposite connection end through which fluid product is supplied to the dispensing orifice; and a porous material part that absorbs fluid product by capillarity, the porous material part disposed between the plunger tube and the dispensing orifice, and having a discharge end located in the immediate vicinity of the dispensing orifice so that actuation of the actuation wall forces a mixture of the fluid product and a gas to be discharged from the dispenser as the sprayed jet; and wherein the discharge end is in contact with the dispensing orifice.

11. The dispenser according to claim 1, wherein the porous material part is one of a foam and fiber that defines an internal network of ducts.

12. The dispenser according to claim 10, wherein the porous material part is one of a foam and fiber that defines an internal network of ducts.

13. The dispenser according to claim 10, wherein the connection end of the plunger tube is in contact with the porous material part.

14. The dispenser according to claim 10, wherein the dispensing orifice is formed by an end piece installed on the opening of the reservoir, the end piece forming a reception housing in which the porous material part fits; and wherein the end piece comprises a body defining a dispensing end forming the dispensing orifice and an opposite attachment end provided with an attachment sleeve to which the tube is connected, the inside of the body forming the reception housing for the porous material part, the housing and the sleeve aligned with each other such that the connection end of the plunger tube can contact the porous material part.

* * * * *